United States Patent [19]

Frey et al.

[11] Patent Number: 4,988,359

[45] Date of Patent: Jan. 29, 1991

[54] FIXING STEM FOR AN ENDOPROSTHESIS

[75] Inventors: Otto Frey, Winterthur; Koch: Rudolf, Berlingen, both of Switzerland

[73] Assignee: Sulzer Brothers Limited, Winterthur, Switzerland

[21] Appl. No.: 392,776

[22] Filed: Mar. 11, 1989

[30] Foreign Application Priority Data

Aug. 23, 1988 [CA] Canada .................................. 3128/88

[51] Int. Cl.⁵ .......................... A61F 2/32; A61F 2/28
[52] U.S. Cl. ........................................ 623/23; 623/16
[58] Field of Search ................. 623/16, 18, 19, 20, 623/22, 23

[56] References Cited

U.S. PATENT DOCUMENTS 4,064,567 12/1977 Burstein ................................ 3/1.91
4,314,381 2/1982 Koeneman ............................ 623/23
4,718,909 1/1988 Brown .................................. 623/16

FOREIGN PATENT DOCUMENTS 0178650 4/1986 European Pat. Off. .

Primary Examiner—David J. Isabella
Attorney, Agent, or Firm—Kenyon & Kenyon

[57] ABSTRACT

The stem of the prosthesis is fixed in a medullated bone by means of a plurality of spacers which are distributed over the length of the stem. The spacers serve to stabilize the stem over the entire length of the stem within the bone cavity. Bone cement is charged into each peripheral opening defined between a pair of spacers via bores drilled transversely through the cortex of the bone in stages from the distal end toward the proximal end.

10 Claims, 1 Drawing Sheet

FIXING STEM FOR AN ENDOPROSTHESIS

This invention relates to a fixing stem for an endoprosthesis. More particularly, this invention relates to a fixing stem for an endoprosthesis for fixing in a medullated bone by means of bone cement bed. Still more particularly, this invention relates to a method of implanting a fixing stem of an endoprosthesis in a bone.

Heretofore, it has been known to mount a stem of an endoprosthesis within a medullated bone by means of a spacer and to fix the stem in place by means of a bone cement bed. In such cases, the stem has been held in a predetermined position relative to the wall of a bone cavity by a spacer which has been pushed onto the stem. For example, U.S. Pat. No. 4,064,567 describes a woven basket which can be placed over the stem of a prosthesis in order, in part to space the stem from a bone cavity wall to provide space for a subsequent injection of a bone cement. U.S. Pat. No. 4,718,909 describes a method and apparatus for cementing a femoral stem prosthesis within a femoral canal which utilizes a spacer to space the stem from a cortical bone of the femur. In some cases, the spacer may be made of a cement permeable resilient structure to permit the passage of bone cement. In such constructions, the spacer element is effective to keep the distal end of the stem in a bone cement bed in a particular position relative to the wall of the operation cavity.

However, the known spacers cannot satisfactorily center a stem over a full height. In this respect, full-height centering is necessary when a cementing technique is used wherein the stem is retained in a particular position in an empty cavity and the bone cement is pressed into place only after the stem has been introduced. In this case, the pressing-in of the cement occurs in stages over the shaft height from the distal zone to the proximal zone. In this case, the bone cortex is formed with lateral bores to permit the pressing in of the bone cement.

Accordingly, it is an object of the invention to permit a fixing stem to be retained and stabilized over the entire length within a bone cavity for transverse reception of a bone cement.

It is another object of the invention to be able to maintain the position of a stem within a bone cavity during pressing-in of a bone cement in stages transversely of the bone and stem.

Briefly, the invention provides a fixing stem for an endoprosthesis with a plurality of peripherally closed spacers which are longitudinally spaced along and peripherally about the stem for spacing the stem from a medullated bone. The spacers serve to define a plurality of peripheral spaces between the stem and the bone in order to individually receive a transversely delivered charge of bone cement therein.

The peripherally closed spacers can be, for example, simply pushed onto the stem and retained thereon by clamping or possibly fixed to the stem, for example, by welding. These spacers ensure that the stem remains in a required position over the entire height relative to the wall of the operation cavity during the introduction of the stem and until the bone cement has cured. This position is determined by the bone cement bed thicknesses necessary at the individual places of the bone cavity. Advantageously, to enable these cement bed thicknesses to be different in different wall zones, the spacers which are disposed at different heights of the stem have different spacing widths and/or the spacing width of a spacer varies in the peripheral direction.

In one construction which has proved satisfactory, the spacers are in the form of intra-operatively deformable wire meshes comprising one or more layers. Advantageously, the spacers may have a trough-shaped cross-section having an opening facing in a proximal direction of the stem.

These and other objects and advantages of the invention will become from the following detailed description taken in conjunction with the accompanying drawings wherein.

Figure 1:
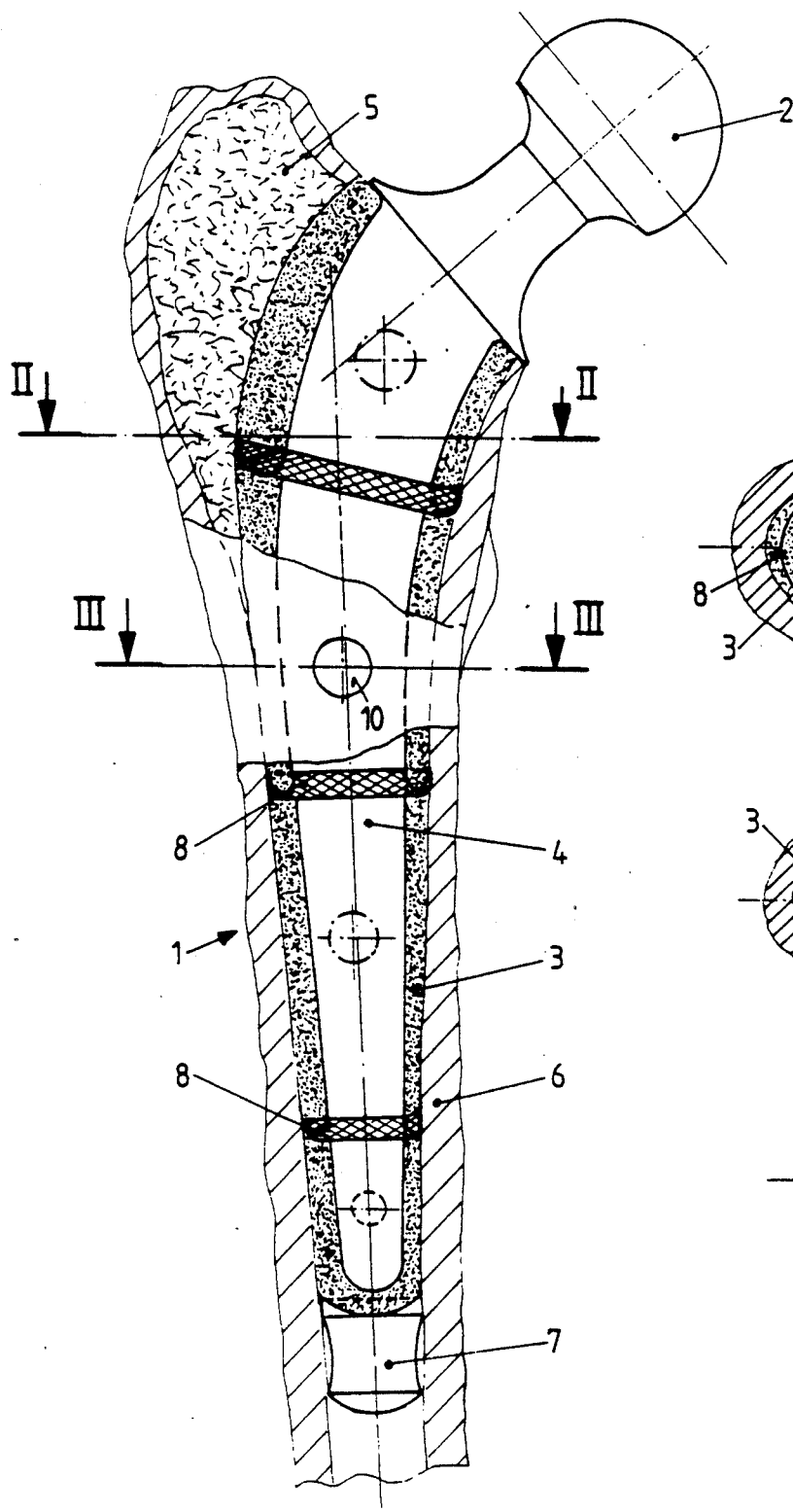
FIG. 1 illustrates a longitudinal section through a proximal zone of a femur bone in which a stem is to be implanted in accordance with the invention.

Referring to FIG. 1, a femur 1 which is prepared operatively with a medullated cavity receives a femoral head prosthesis 2 which is secured in place by a bone cement bed 3. The bone cavity may have been contrived by evacuation of the spongy tissue 5 as far as the edge of the hard cortex 6 and is closed in the distal direction by a marrow cavity barrier or plug 7. In addition, a plurality of peripherally closed spacers 8 are longitudinally spaced along and peripherally about a stem 4 of the prosthesis 2 for spacing the stem 4 from the cortex 6 of the bone. As indicated, the spacers 8 are disposed at different heights from the distal zone towards the proximal zone and are secured, for example, by clamping or welding, to the stem 4 at predetermined heights. The spacers 8 serve to stabilize the stem 4 in the evacuated empty femur 1 before introduction of the bone cement 3. Further, the spacers 8 define a plurality of peripheral spaces between the stem 4 and the cortex 6.

Figure 2:
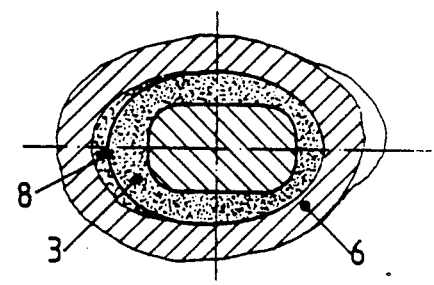
FIG. 2 illustrates a view taken on line II—II of FIG. 1.

As illustrated, the spacers 8 are embodied by braided or woven metal wire meshes which have a trough-shaped cross section with an opening facing in a proximal direction of a stem. In addition, the spacing between the individual spacers 8 may vary and be non-uniform. Likewise, each spacer 8 may have a variable peripheral width. These characteristics serve the ensure that different cement bed thicknesses may be accommodated over the height of the stem 4 and around the stem periphery as indicated in FIG. 2.

Figure 3:
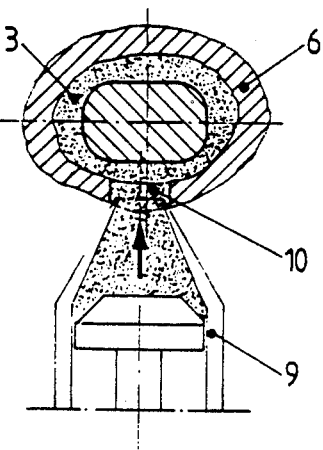
FIG. 3 illustrates a view taken on line III—III of FIG. 1.

Referring to FIGS. 1 and 3, the cortex 6 is provided with a plurality of longitudinally spaced bores 10 which are formed in the bone 1 with each bore 10 communicating with a respective peripheral space defined between a pair of spacers 8. As indicated in FIG. 3, a suitable cement injector 9 is used for the deliverance of bone cement transversely through each bore 10 into a respective space.

During an operation, for example, after the cement barrier 7 is put in place, the stem 4 of the prosthesis 2 with the spacers 8 thereon is positioned in the cavity of the bone 1. Thereafter, the bores 10 are drilled through the cortex 6 of the bone in alignment with the spaces which are defined between each pair of spacers 8. As indicated in FIG. 3, a charge of bone cement is then delivered transversely into each peripheral space starting from the distal end and proceeding in stages towards the proximal end. Upon curing of the bone cement, the stem is firmly fixed in place.

What is claimed is:

1. In combination
   a fixing stem for an endoprosthesis for fixing in a medullated bone; and
   a plurality of peripherally closed spacers of wire mesh longitudinally spaced along and peripherally about said stem for spacing said stem from a medullated bone to define a plurality of peripheral spaces between said stem and the bone to individually receive a transversely delivered charge of bone cement therein.

2. The combination as set forth in claim 1 wherein each spacer is deformable.

3. The combination as set forth in claim 1 wherein each spacer is of trough-shaped cross-section having an opening facing in a proximal direction of the stem.

4. The combination as set forth in claim 1 wherein said spacers are disposed in non-uniform spaced relation from each other.

5. The combination as set forth in claim 4 wherein at least one spacer has a variable peripheral width.

6. The combination as set forth in claim 1 wherein at least one spacer has a variable peripheral width.

7. In combination
   a fixing stem for an endoprosthesis; and
   a plurality of peripherally closed spacers of deformable wire mesh spaced longitudinally of said stem to space said stem from a medullated bone to define a plurality of peripheral spaces between said stem and the bone to individually receive a transversely delivered charge of bone cement.

8. The combination as set forth in claim 7 wherein each spacer has a trough-shaped cross-section having an opening facing in a proximal direction of said stem.

9. The combination as set forth in claim 8 wherein at least one spacer has a variable peripheral width.

10. The combination as set forth in claim 8 wherein said spacers are disposed in non-uniform spaced relation from each other and at least one spacer has a variable peripheral width.

* * * * *

UNITED STATES PATENT AND TRADEMARK OFFICE
CERTIFICATE OF CORRECTION

PATENT NO. : 4,988,359

DATED : January 29, 1991

INVENTOR(S) : OTTO FREY, et al

It is certified that error appears in the above-identified patent and that said Letters Patent is hereby corrected as shown below:

ON TITLE PAGE:[22] change "Mar. 11, 1989" to -Aug. 11, 1989-
  Line 30 change "[CA] Canada" to -[CH] Switzerland- Signed and Sealed this First Day of September, 1992

Attest:

DOUGLAS B. COMER

*Attesting Officer*      Acting Commissioner of Patents and Trademarks